United States Patent
Maglione et al.

(10) Patent No.: US 7,314,734 B2
(45) Date of Patent: *Jan. 1, 2008

(54) MUTEINS OF PLACENTAL GROWTH FACTOR TYPE 1, PREPARATION METHOD AND APPLICATION THEREOF

(76) Inventors: Domenico Maglione, Via della Peschiera 20, 03012 Anagni FR (IT); Mauro Battisti, Viale degli Eroi 16, 00032 Carpineto RM (IT); Ettore Conti, Via Toscana 1 - Res. "Colli del Vivaro" 40, 03012 Rocca di Papa RM (IT); Giuseppe Salvia, Via Andrea Doria 39, 95123 Catania CT (IT); Marina Tucci, Via Sanitá 40, 03012 Anagni FR (IT); Alberto Mion, Via Tibertina 191, 03100 Frosinone FR (IT)

( * ) Notice: Subject to any disclaimer, the term of this patent is extended or adjusted under 35 U.S.C. 154(b) by 0 days.

This patent is subject to a terminal disclaimer.

(21) Appl. No.: 10/514,707

(22) PCT Filed: May 19, 2003

(86) PCT No.: PCT/IT03/00296

§ 371 (c)(1),
(2), (4) Date: Jan. 7, 2005

(87) PCT Pub. No.: WO03/097688

PCT Pub. Date: Nov. 27, 2003

(65) Prior Publication Data

US 2005/0176634 A1   Aug. 11, 2005

(30) Foreign Application Priority Data

May 17, 2002   (IT) ......................... RM2002A0277

(51) Int. Cl.
*A61K 38/18*   (2006.01)
*C12P 21/00*   (2006.01)
*C12P 21/02*   (2006.01)

(52) U.S. Cl. .................... 435/69.1; 530/350; 530/399; 514/12; 435/69.4; 435/320.1; 435/252.8; 435/6; 435/91.2; 536/23.5; 536/24.1

(58) Field of Classification Search ..................... None
See application file for complete search history.

(56) References Cited

U.S. PATENT DOCUMENTS 5,994,300 A * 11/1999 Bayne et al. ................. 514/12

FOREIGN PATENT DOCUMENTS

| WO | WO 92/06194 | * | 4/1992 |
| WO | WO 01/85796 | * | 11/2001 |

OTHER PUBLICATIONS

Wells, 1990, Biochemistry 29:8509-8517.*
Ngo et al., 1994, The Protein Folding Problem and Teritary Structure Prediction, pp. 492-495.*
Errico et al. J Biol Chem. 2004;279: 43929-39.*
Saragovi & Burgess, Exp Opin Ther Patents. 1999; 9: 737-751, p. 739, left column, 2nd paragraph.*
Cao et al. Biochem Biophys Res Comm. 1997; 235: 493-498.*

* cited by examiner

*Primary Examiner*—Eileen O'Hara
*Assistant Examiner*—Christina Borgeest
(74) *Attorney, Agent, or Firm*—Joseph Fischer; Beusse, Wolter, Sanks, Mora & Maire, P.A.

(57) ABSTRACT

The present invention relates to chemically stable muteins of type 1 Placental Growth Factor (PLGF-1) bearing the substitution or elimination of a cysteine residue from the wild type protein amino acid sequence, their preparation, their therapeutic and cosmetic uses, and pharmaceutical and cosmetic compositions containing said derivatives. The invention likewise relates to the production of antibodies for said derivatives and their use in the diagnosis and treatment of tumoral and non-tumoral pathologies.

26 Claims, 6 Drawing Sheets

MUTEINS OF PLACENTAL GROWTH FACTOR TYPE 1, PREPARATION METHOD AND APPLICATION THEREOF

CROSS-REFERENCE TO RELATED APPLICATIONS

This application is a National Stage entry under 35 USC 371 of International Application No. PCT/IT03/00296, filed May 19, 2003, which claims priority to Italian Application No. RM2002A000277, filed May 17, 2002.

1. Field of Invention

The present invention relates to stable muteins of type 1 Placental Growth Factor (PLGF-1), their preparation, their therapeutic and cosmetic use and pharmaceutical and cosmetic compositions containing said derivatives. The invention likewise relates to the production of antibodies to said derivatives and their use in the diagnosis and treatment of tumoral and non-tumoral pathologies.

2. State of the Art

Type 1 Placental Growth Factor (PLGF-1) is an angiogenic homodimeric glycoprotein. Angiogenic activity relates to the dimeric form, as the monomeric form is inactive. The complete polynucleotide sequence encoding the PLGF-1 protein, along with its polypeptide sequence, were described by Maglione and Persico in Pat. EP-B-0 550 519 (WO-A-92/06194).

The above patent describes a method for producing PLGF-1 in bacteria modified using an inducible expression system, said method involving, after induction, bacterial lysis and direct extraction of the raw protein from the lysate solution. The protein obtained in this way shows low levels of biological activity.

A method for extraction and purification of the raw placental factor, obtained by expression in bacteria, is described by Maglione et. al. in patent application PCT/IT02/00065. The method involves a series of extraction, renaturation and purification passages, which as a whole make it possible to obtain the pure protein in an essentially dimeric form, that is to say in its most active form. It is, in fact, known that the monomeric form of the protein is biologically inactive, and only acquires angiogenic functions after renaturation to the dimeric form.

However, the present inventors have observed that the protein in dimeric form is partially unstable, and gives rise, in an aqueous solution, during storage or processing, to multimeric forms that show less biological activity and for this reason are less suitable for therapeutic use, due to the uncertainty of doses and biological activity.

The aim of the present invention is therefore to solve the problem of poor chemical/biological stability of PLGF-1 as observed mainly when the latter is conserved in aqueous solutions.

SUMMARY OF THE INVENTION

The invention is based on the unexpected discovery that derivatives of the natural protein PLGF-1 with modifications in their polypeptide sequence, specifically involving substitution or elimination of at least one cysteine residue, show greatly increased chemical stability, while at the same time maintaining their original biological activity essentially unchanged. In the light of this discovery, a first object of the application is represented by a mutein of the monomeric form of type 1 human or animal Placental Growth Factor (PLGF-1) comprising substitution or elimination in the wild type protein polypeptide sequence of at least one of the nine cysteine residues (Cys) contained therein. Said substitution or elimination does not affect the dimerisation process essential to obtain the protein in its biologically active form, but prevents multimerisation of the monomeric form.

Among the various cysteine residues, it has been seen that elimination or substitution of a residue present in the C-terminal portion, and specifically in position 142 of the complete polypeptide sequence, that is to say comprising both the mature PLGF-1 protein and the corresponding signal peptide, is particularly effective. In the preferred embodiment of the invention the residue Cys 142 is replaced by a glycine residue (Gly). This substitution produces a mutein of the monomeric form of PLGF-1 that has unchanged dimerisation capacity, but is basically incapable of generating multimerisation products. As well as the modifications described above, the muteins according to the invention may contain further eliminations, substitutions or additions of one or more wild type protein amino acids, providing said modifications do not alter the functional characteristics of the mutein itself.

A second object of the invention is therefore represented by a mutein of the factor PLGF-1 in dimeric form, preferably purified in such a way as essentially to comprise the dimer alone. Said mutein may equally well be the mature protein or the pre-protein, comprising a signal peptide in the N-terminal portion.

A further object of the invention is the nucleotide sequence comprising the DNA encoding the mutein in suit. The sequence is characterised in that a TGC or TGT codon encoding the amino acid cysteine in the natural PLGF-1 sequence is eliminated or modified. In a preferred embodiment of the invention the codon corresponding to cysteine is substituted by a GGC, GGT, GGA or GGG codon, all encoding the amino acid glycine (Gly). It is preferably the thymidine base (T) in position 382 (TGC codon) of sequence SEQ ID NO:1 that is replaced by the guanidine base (G) to generate the GGC codon.

A further object of the invention is an expression system comprising the nucleotide sequence seen above, flanked by untranslated sequences controlling and regulating expression. This system can be induced in prokaryotic cells, preferably bacterial cells.

Expression is under the control of an inducible promoter and can be induced by means of suitable compounds. Host cells modified using the expression system seen above are also the object of the invention. These are prokaryotic cells, preferably bacterial cells such as *E. coli*. The invention also covers processes for production of the nucleotide sequence, in which the DNA encoding the mutein is produced by polymerase chain reaction (PCR) using as a primer oligonucleotides that have been suitably modified with respect to the wild type protein sequence. Preferably the oligonucleotide of SEQ ID NO:3 is used as 5'-3' forward primer and the oligonucleotide of sequence SEQ ID NO:4 is used as 5'-3' reverse primer.

A further object of the invention is a process for production and extraction of the mutein in which host cells, preferably bacterial, modified using the expression system according to the invention, are cultivated in a suitable culture medium, expression of the protein is induced by a suitable inducer, the cells are isolated and lysated and the mutein is extracted from the lysis mixture. During the fermentation step and before the induction of the expression step, the cells are cultivated until a high optical density (O.D.) of the culture medium is reached. Expression of the protein is subsequently induced by addition of suitable induction agents. During the subsequent steps the cells are lysated, to release the endocellular materials into the culture medium, specifically nucleic material and inclusion bodies, the latter are solubilised and the protein obtained in this way is renatured in dimeric form. The extraction and purification process may comprise additional optional steps for purification of the dimeric protein. In a preferred embodiment the process comprises at least one additional purification step on ionic exchange or reverse phase chromatography. In a further embodiment the process comprises an initial anionic exchange chromatography purification followed by reverse phase chromatography.

The mutein obtained using the production, extraction and purification process according to the invention contains not less than 98.5% active protein and not more than 1.5% of the monomeric form. The active form essentially consists of the dimeric form, and contains only traces of the multimeric form. Stability tests underline the high stability during storage and during processing typical of the mutein in dimeric form.

(M) indicates the molecular weight references; (1) indicates the PlGF-1CG (3 micrograms) solubilised in the physiologic solution at a concentration of 20 mg/ml and frozen (control); (2) indicates the PlGF-1CG (3 micrograms) solubilised in the physiologic solution at a concentration of 20 mg/ml and stored at 4-8° C. for 40 days.

Figure 2:
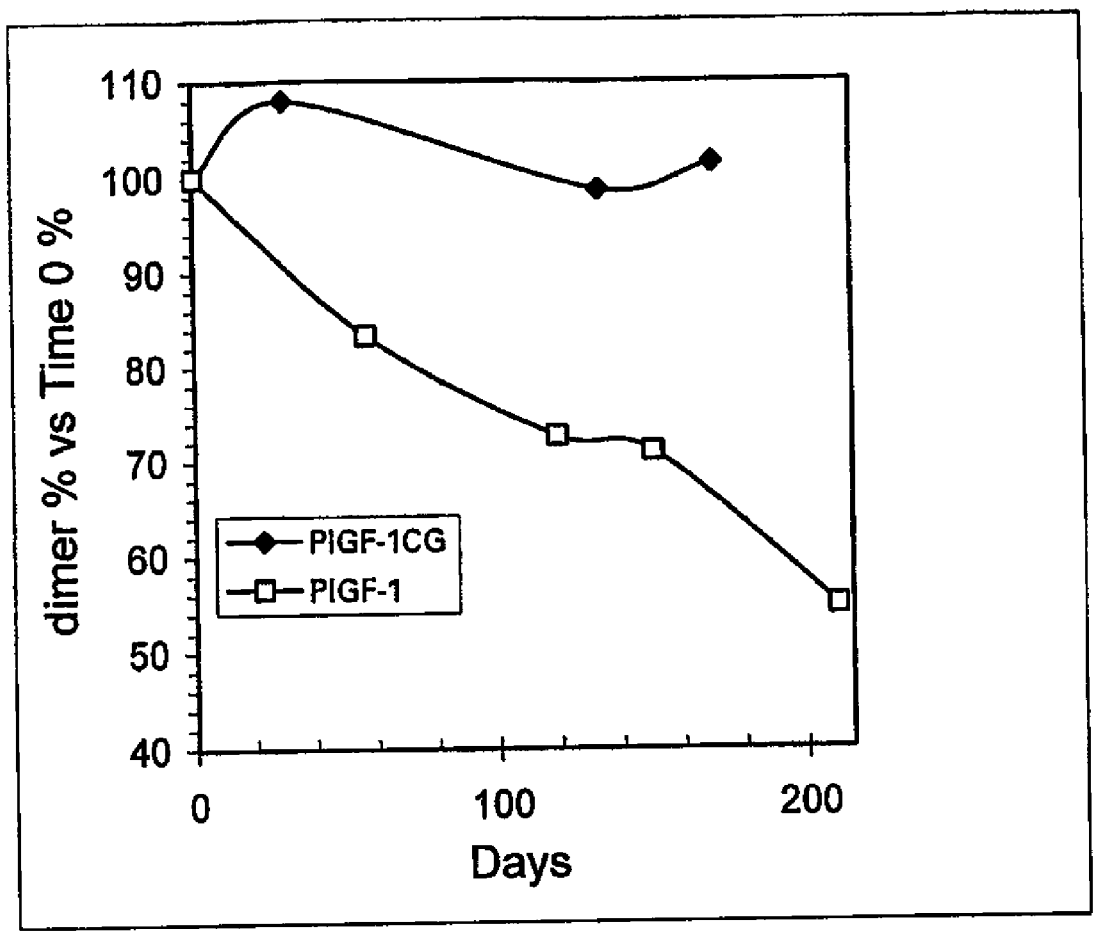

FIG. 2: The figure shows the data from table 2 expressed in graph form.

Figure 3:
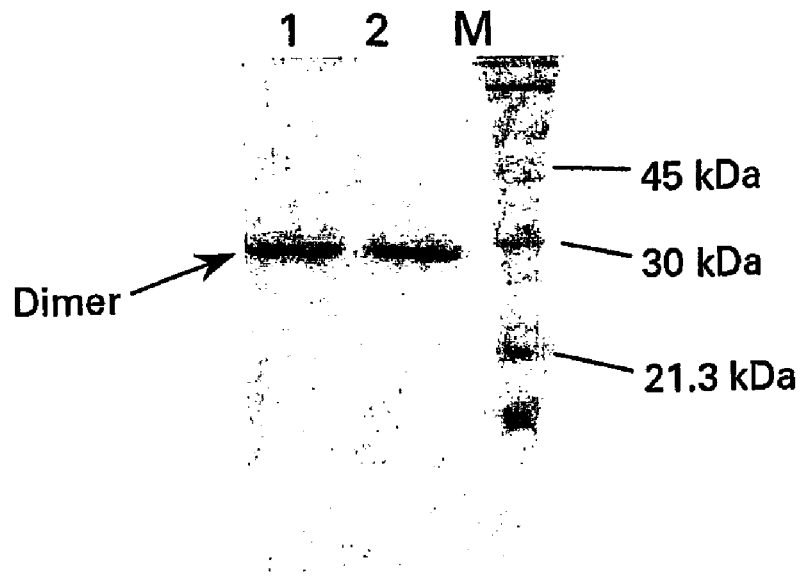

FIG. 3: The figure shows the SDS-PAGE electrophoretic profile of the mutein PLGF-1CG solubilised in Carbopol gel at 0.2 mg/ml and stored at 4-8° C. for 170 days. (M) indicates the molecular weight references; (1) indicates the PlGF-1CG (2 micrograms) solubilised in Carbopol gel at a concentration of 0.2 mg/ml and stored at 4-8° C. for 170 days; (2) indicates the PlGF-1CG (2 micrograms) solubilised in Carbopol gel at a concentration of 0.2 mg/ml and frozen (control).

Figure 4:
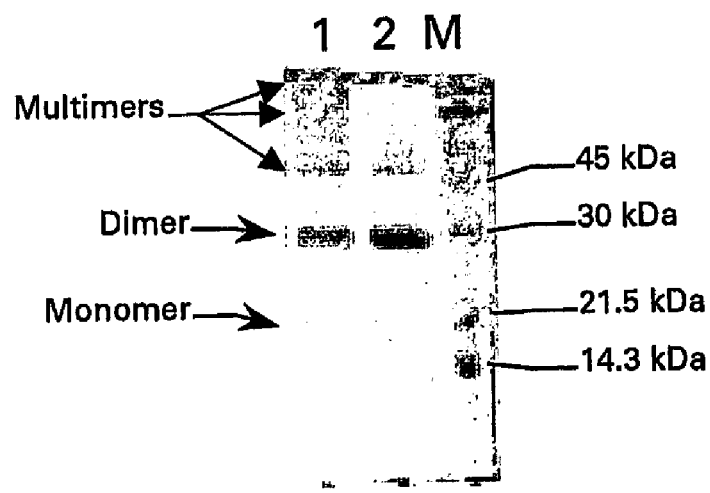

FIG. 4: The figure shows the SDS-PAGE electrophoretic profile of the native form of PLGF-1 solubilised in Carbopol gel at 0.2 mg/ml and stored at 4-8° C. for 150 days. (M) indicates the molecular weight references; (1) indicates the PLGF-1 (2 micrograms) solubilised in Carbopol gel at a concentration of 0.2 mg/ml and stored at 4-8° C. for 150 days; (2) indicates the PlGF-1 (2 micrograms) solubilised in Carbopol gel at a concentration of 0.2 mg/ml and frozen (control).

Figure 5:
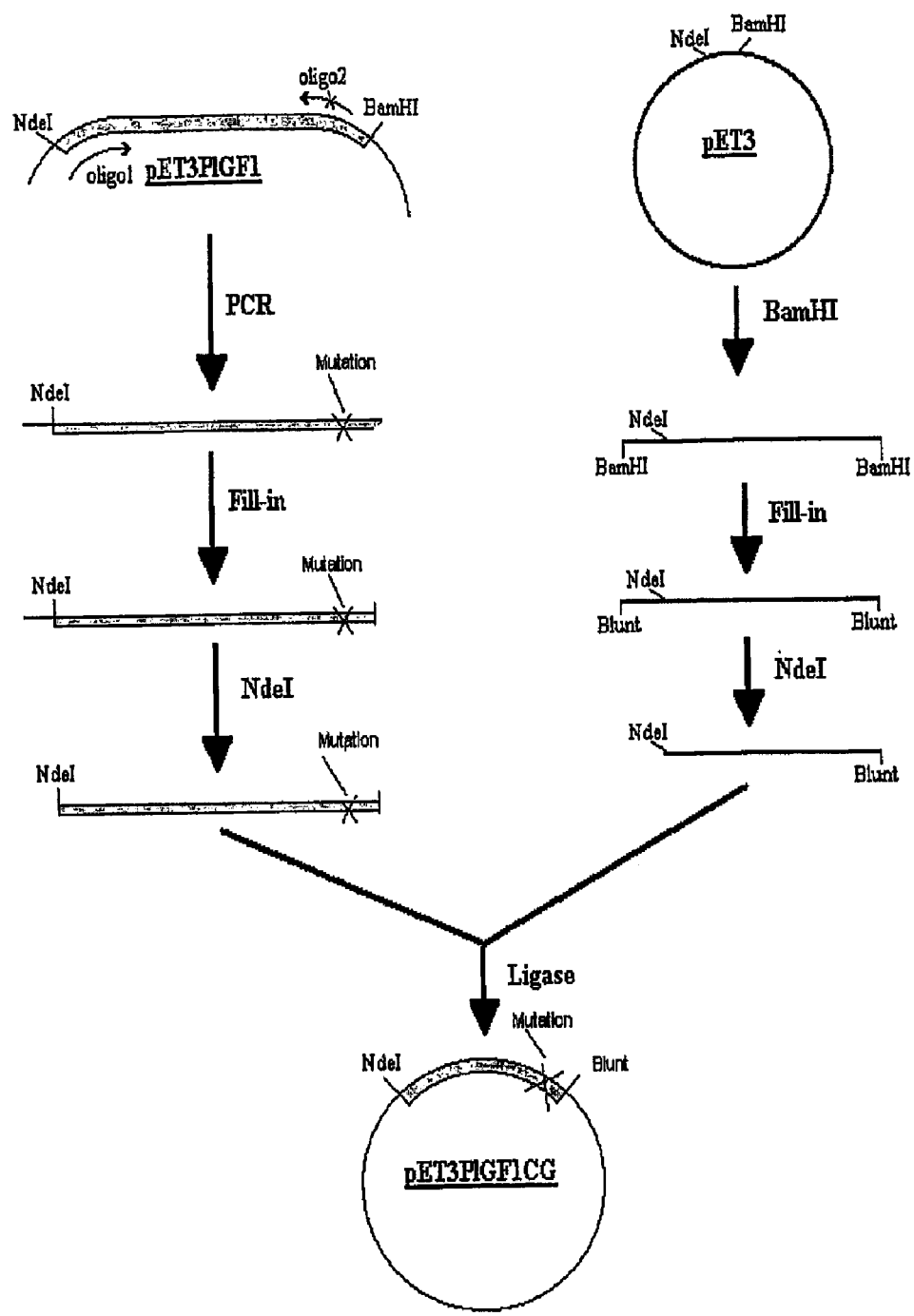

FIG. 5: The figure is a schematic illustration of the process for construction of the plasmid pET3PLGF1CG, coding the PLGF-1 mutein denominated PLGF-1CG.

Figure 6:
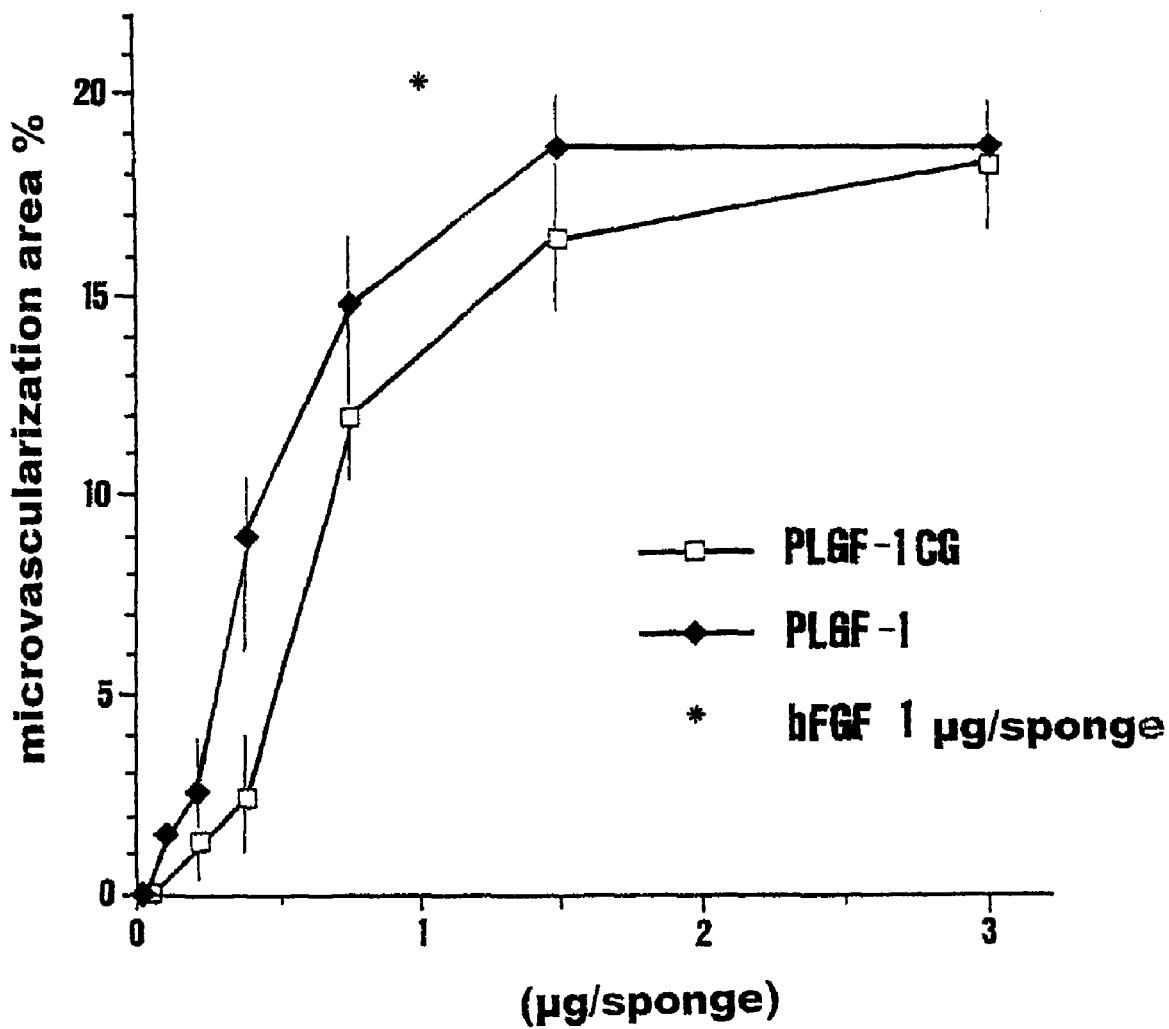

FIG. 6: The figure shows the angiogenic activity of wild type PLGF-1 and of the mutein PLGF-1CG at increasing concentrations of substance. The activity of the basic fibroblast growth factor bFGF is indicated as a reference.

Figure 7:
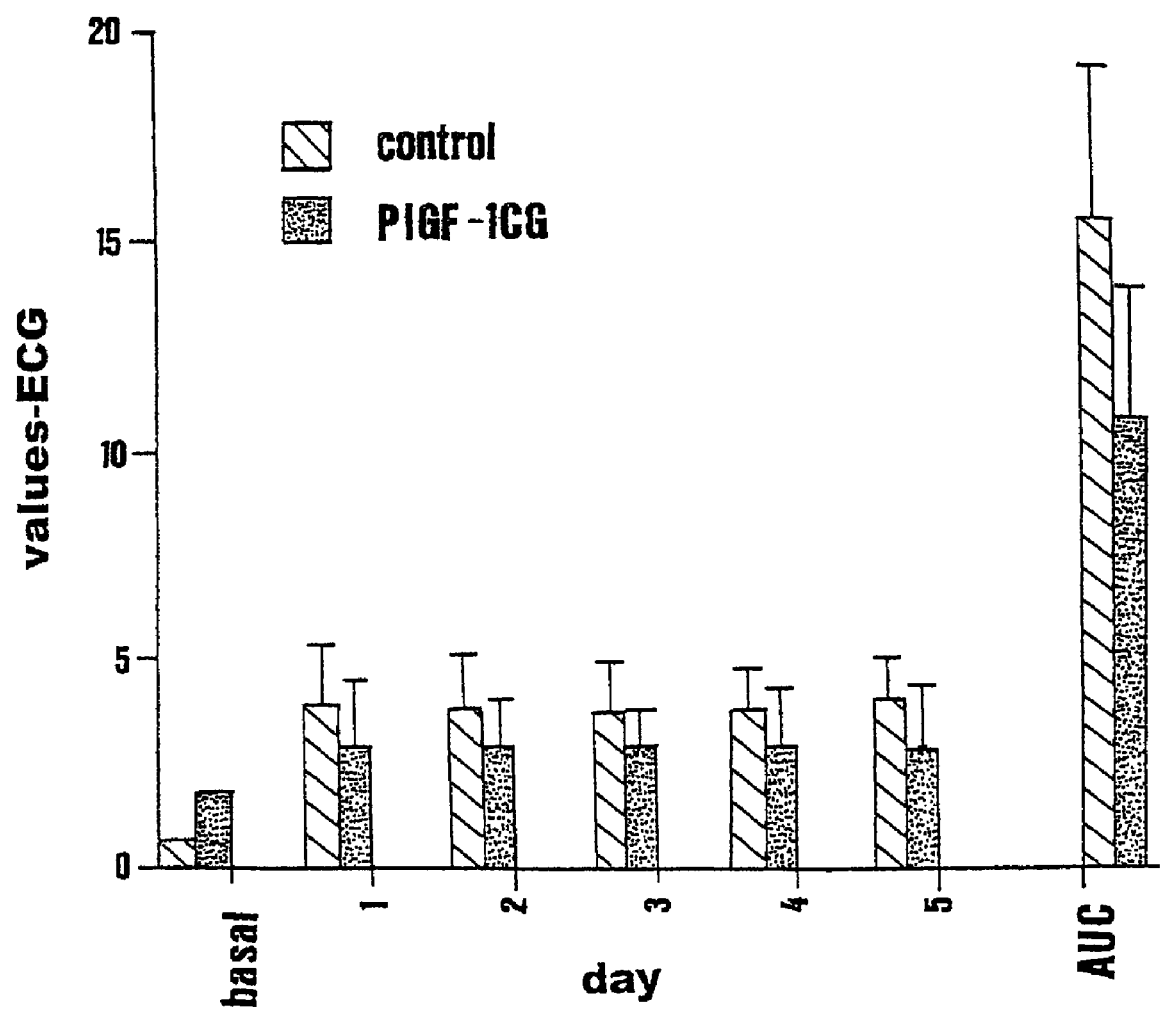

FIG. 7: The figure shows the effect of the mutein PLGF-1CG on isoprenaline-induced ischemic damage to cardiac tissue in rabbit. The x axis indicates the days treatment and the value AUC representing the total area included within the curve identified by the daily ECG scores.

SEQUENCE LIST

SEQ ID NO:1 nucleotide sequence for wild type PLGF-1 without signal peptide.

SEQ ID NO:2 nucleotide sequence for natural PLGF-1.

SEQ ID NO:3 sequence for the oligonucleotide used as forward primer in the PCR.

SEQ ID NO:4 sequence for the oligonucleotide used as reverse primer in the PCR.

DETAILED DESCRIPTION OF THE INVENTION

The complete polypeptide sequence of the human factor PLGF-1 of 149 amino acids, along with a fragment of cDNA of 1645 nucleotides comprising the sequence encoding the factor PLGF-1, are indicated in the patent EP-B-0 550 519. A freely accessible plasmid containing the nucleotide sequence of 1645 bases has also been filed with ATCC under ATCC filing number 40892.

The sequence encoding the pre-protein is comprised between positions 322 and 768 and is indicated in this application as SEQ ID NO:1.

Wild type PLGF-1 in pre-protein form is a polypeptide with 149 amino acids comprising a signal peptide of 18 amino acids in the N-terminal portion. The sequence for the mature protein, delimited by positions 19 and 149, is indicated in this application as SEQ ID NO: 2. Said sequence comprises 9 cysteine residues (Cys) located in positions 35, 60, 66, 69, 70, 77, 111, 113 and 125.

In the muteins according to the invention, at least one of said cysteine residues is eliminated or substituted by another residue, the only condition being that the mutation does not significantly affect or eliminate the ability of the mutein in its monomeric form to generate the biologically active and therapeutically useful dimeric form. Experimental data has shown that the eliminated or substituted residue must for preference be located in the C-terminal portion of the protein, and that the optimum residue for the purpose of the invention is the one in position 125.

Muteins of the wild type placental growth factor can be produced by synthesis using polymer synthesis techniques known from the literature. However the preferred method is expression of the protein in genetically modified host cells. For this purpose the host cells are transformed by introducing a cloning vector and/or an expression vector comprising an insert that corresponds to the PLGF-1 gene after suitable modification.

Preparation of the DNA encoding the muteins according to the invention is carried out by site-specific mutagenesis and implies point mutation in codons corresponding to cysteine, that is to say TGC or TGT. These mutations may be deletions or substitutions of one or more bases, without causing reading frame shift downstream of the mutation. In the case of deletion a complete codon must therefore be removed. Preferably, site specific mutation is a point substitution of a base in a cysteine codon, with consequent formation of a new codon. In this sense the mutation will result in substitution of a cysteine residue with another amino acid residue.

Various known techniques of site-specific mutagenesis can be used to prepare the cDNA encoding the required mutein.

Methods that can be used are, for example, mutagenesis obtained with oligonucleotides (Adelman et al. *"DNA"*

2:183, 1983), PCR mutagenesis (Leung et al. *Technique* 1:11-15, 1989) or cassette-mutagenesis (Wells et al. *Gene* 34:315, 1985).

In the preferred embodiment of the invention, synthesis of the mutant DNA is carried out using the mutation technique through polymerase chain reaction (PCR). The cDNA encoding the wild type type PLGF-1 factor described in literature or any equivalents thereof caused by degeneration of the genetic code was used as a template for the PCR. Preferably, only the portion encoding the methionilated protein in the N-terminal position with or without signal peptide will be used; for example the sequence reported in the present application as SEQ ID NO:1 or equivalents thereof, comprised in the expression vector pET3PlGF-1 corresponding to the protein without the signal peptide. The oligonucleotide 5'-3' (forward) complementary to the region encoding the N-terminal portion of the protein, and the oligonucleotide 5'-3' (reverse) complementary to the region of the sequence comprising the cysteine codon to be mutated were used as primers for the PCR. The latter oligonucleotide will contain the base substitution or substitutions necessary to introduce the mutation required. The primers used may equally contain additional bases in the 5' and/or 3' terminal regions to introduce restriction sites suitable to isolate and purify the mutated sequence.

The codon corresponding to the cysteine residue may be substituted by a codon encoding any neutral amino acid, whether polar such as Ser, Thr, Gln, or Asn, or non-polar such as Gly, Ala, Val, Ile or Leu. Preferred amino acids are Gly and Ala.

In the preferred embodiment the forward primer is represented by the sequence identified as SEQ ID NO: 3, while the reverse primer is represented by the sequence SEQ ID NO: 4. The latter comprises a T→G substitution in position 382 of sequence SEQ ID NO: 1, a substitution that transforms the TGC codon of the cysteine in position 125 of the sequence SEQ ID NO:4 into a GGC codon corresponding to a glycine.

The suitably modified cDNA is subsequently cut and inserted into an expression vector under the control of a suitable inducible system compatible with the host cell.

Preferably, inducible expression systems compatible with prokaryotic cells are used. Examples of these systems are:

pBAD expression system (In vitrogen BV) in which protein synthesis is placed under the control of the araBAD promoter and can be induced in various strains of *E.coli* using arabinose;

T7 Expression System (In vitrogen BV or Promega) in which protein synthesis is controlled by the RNA polymerase promoter for phage T7 and can be induced using lactose, isopropyl-β-D-thiogalactopyranoside (IPTG) or derivatives or functionally equivalent analogous thereof. In this case it is necessary to use type DE3 (B121(DE3) or JM109(DE3)) derivatives of *E.coli*, that is to say ones that contain a copy of the gene for phage T7 Rna polymerase placed under the control of a lactose-inducible promoter;

Trc expression system (In vitrogen BV)in which protein synthesis is placed under the control of the hybrid promoter trc. This promoter has been obtained by fusion of the trp promoter with lac promoters and it can be induced in various strains of *E.coli* by means of lactose or similar equivalents thereof(IPTG);

Tac expression system (Amersham biosciences) in which protein synthesis is placed under the control of the tac promoter. In this system, protein synthesis is induced in strains of *E.coli* lacIq (type LM105) by means of lactose or similar equivalents thereof(IPTG);

$P_L$ expression system in which protein synthesis is placed under the control of the $P_L$ promoter and may be induced by the addition of tryptophan. In this case the use of *E.coli* derivatives (GI724) containing a copy of the gene encoding the cI repressor of the Lambda phage is required, under the control of a tryptophan-inducible promoter.

It is obviously possible to express the modified cDNA encoding the mutein in eukaryotic host cells derived from yeast or from multicellular organisms. In this case an expression system compatible with said cells will be selected.

In the preferred embodiment of the invention expression is carried out under the control of the T7 phage RNA polymerase system and induced with isopropyl-β-D-thiogalactopyranoside.

The expression vector also comprises additional sequences encoding the normal functions necessary for cloning, selection and expression, such as selective markers and/or a polyadenylation site and/or a transcription regulating sequence.

Host cells are therefore transformed, using standard techniques well known to the man skilled in the art, with the expression vector containing the cDNA encoding the mutein required. These cells may be prokaryotic, eukaryotic, animal, human or plant cells, in particular bacterial cells, such as *E.coli* or *Bacillus*, yeast cells, such as *Saccharomyces*, or animal cells, such as Vero, HeLa, CHO, COS.

The preferred micro-organism is obtained by integration into the commercially available strain [B12(DE3)pLysS] (Promega Corporation USA) of the gene from a human PLGF-1 mutein.

The modified cells used to produce the muteins according to the invention are stored before use in lyophilised form to preserve their expression capacity. At the time of use, the lyophilised material is re-solubilised using a suitable buffer.

The modified host cells are then cultivated in liquid culture medium. Although a wide range of known culture mediums is commercially available and can effectively be used, the fermentation step in accordance with the invention is preferably carried out in a culture medium free from any material of animal or human origin, in order to avoid any risk of infection. Yeast extracts (Difco) additioned with one or more suitable antibiotics represent the most suitable medium for the process. The fermentation step may be preceded by a pre-inoculation step in which the lyophilised micro-organism is suspended in the culture medium and subjected to consecutive incubation and dilution steps, aimed at obtaining an optimum quantity of micro-organism cells in the culture.

Fermentation is carried out in the culture medium seen above, at a suitable temperature for the micro-organism, normally approximately 37° C., in the presence of a percentage of dissolved $O_2$, with respect to the saturation with air, of between 20% and 40%, preferably 30%. The pH during culture is maintained at optimum values for the micro-organism being used, which will normally be neutral or very slightly acid or alkaline (6.4 to 7.4). Furthermore, given that the fermentation process takes place under stirring, the use of anti-surfactants is advantageous.

As fermentation progresses it is accompanied by an increase in the optical density of the culture medium. Therefore the optical density at 600 nm is the parameter used according to the invention to monitor the progress of the process. The cellular and therefore optical density reached in the culture at the time that expression is induced must be sufficiently high to guarantee a high yield of expressed protein. Although optical densities at 600 nm ($OD^{600}$) higher than 0.2 can already be used, optical densities of up to 50 can be obtained thanks to the culture mediums employed. Densities exceeding 18 are preferable in order to obtain high mutein production levels. Densities of between 16 and 20 have given optimum results. Fermentation is then maintained at the conditions seen above until these optical density values are reached, then expression of the protein is induced.

Any agent or chemical-physical condition capable of inducing the heterologous mutein expression mechanisms in the cells of the micro-organisms being used may be employed. In the specific case that the bacterial strain BL21(DE3)pLysS modified with an expression plasmid containing the T7 phage promoter is used, expression is induced with lactose or derivatives thereof, such as isopropyl-β-thiogalactopyranoside (IPTG) in a suitable concentration, that is to say approximately 1 mM. The duration of the induction may vary according to requirements. Good results have been obtained for periods of several hours, preferably from 3 to 4 hours; in the optimum process induction is maintained for 3 hours and 20 minutes using a percentage of dissolved $O_2$ equivalent to approximately 10%.

Samples of cells are taken prior to and following induction and subjected to control analytical techniques such as SDS-PAGE electrophoresis, to determine the results of the induction.

When expression of the protein has reached the levels required, the cells are separated from the culture medium, for example by centrifugation, and subjected to an extraction process.

The extraction process foresees an initial cell lysis step. In effect when the mutein is expressed in bacteria, it remains segregated inside the host cell, in the form of inclusion bodies. The lysis process may be carried out using freeze/thaw, French Press, ultrasound (sonication) or similar known techniques, in lysis solutions containing suitable concentrations of surfactants, preferably containing Triton X100 in concentrations of from 0.5% to 1%. The preferred technique when using the bacterial strain BL21(DE3)pLysS is the freeze/thaw technique, which in an optimum embodiment is repeated for at least two consecutive cycles.

Given that the PLGF-1 mutein is released into the lysis medium as expressed by the host cell, that is to say in the biologically inactive monomeric form, lysis is followed by a renaturation step, at least in part, consisting in dimerisation of the monomer. Renaturation of the mutein is obtained by adding suitable concentrations of oxidating-reducing pairs to the diluted solution, followed by an incubation period of from 10 to 30 hours, preferably 18 to 20 hours at a temperature of between 10° C. and 30° C., preferably 20° C. under stirring. Examples of these pairs are: Cystine/Cysteine, Cystamine/Cysteamine, 2-hydroxyethyldisulfide/2-mercaptoethanol or glutathione in oxidised and reduced form. The latter represents the preferred agent and is used, in oxidised form, at a concentration of from 0.1 to 2.5 mM, preferably 0.5 mM and, in reduced form, from 0.25 to 6.25 mM, preferably 1.25 mM.

In the case where the expressed PLGF-1 mutein is released into the lysis medium in the form of inclusion bodies, the renaturation step is receded by a solubilisation passage. The fraction containing the inclusion bodies is solubilised in a denaturing buffer containing know denaturing agents such as urea, guanidine isothiocyanate, guanidine hydrochloride. Preferably, the denaturing solution is a solution of urea in denaturing concentration, for example 8M. To accelerate the solubilisation process it may be advantageous to subject the fraction containing the inclusion bodies to homogenisation or ultrasound (sonication). The solution containing the protein is subsequently diluted with the denaturing buffer itself and/or with a diluent solution until reaching an optical density measured at 280 nm of approximately 0.5 $OD^{280}$. Suitable dilution solutions contain salts and polyethylenglycol (PEG) and have an alkaline pH (pH approximately 8).

The release of the PLGF-1 mutein into the lysis medium is normally accompanied by the release of the various components and endocellular substances from the micro-organism, above all the nucleic material, which may affect or interfere with the protein purification process. To avoid this problem, the suspension/solution obtained directly from cell lysis may be subjected to an additional optional and preliminary processing step consisting in fragmentation of said material. This result is obtained by means of enzymatic agents, such as DNAses (natural or recombinant such as Benzonase), chemical agents, such as deoxycholic acid, or physical-mechanical agents, such as ultrasound (sonication), rapid stirring with blades, for example in a blender. Physical fragmentation of the DNA is carried out in suitable volumes of washing solution containing chelating agents and detergents, for example EDTA and Triton X100, and is preferably repeated for a number of cycles, alternated with dilution, centrifugation and elimination of the supernatant in order to remove every cellular component or substance from the fraction containing the inclusion bodies.

Although the PLGF-1 mutein after renaturation can already be used as is, it is preferably subjected to at least one purification step using any one of the techniques well known to the man skilled in the art for purification of proteic material. For this purpose, the mutein may be subjected to gel-filtration, ion exchange chromatography, affinity chromatography, HPLC, reverse phase chromatography and/or gel electrophoresis. Preferred techniques are anionic exchange and reverse phase chromatography. When it is necessary to obtain an extremely high level of purification, for example one suitable for therapeutic use, at least two of the techniques mentioned above are combined in sequence.

The solution containing the partially renatured mutein, that is to say at least in part in dimeric form, may be loaded onto anionic exchange resin in order to enrich the mixture with the dimeric form and free it from bacterial contaminants. Any commercially available matrix suitable for anionic exchange chromatography may be used, to the extent that its capacity, load and flow speed characteristics are compatible with an industrial process. In a preferred embodiment a high flow resin, for example Q-sepharose Fast Flow (Amersham biosciences) or an equivalent, is used. The resins used allow ample volumes of proteic solution to be loaded, with a Load Volume/Column Volume ratios varying from 1:1 to 10:1. Vol./Vol. ratios close to 10:1 are preferred, as they enable use of the column to be optimised. The entire chromatography process can advantageously be carried out automatically by a computerised system controlled by a suitable program, for example the FPCL Director Software system (Amersham biosciences).

In a variant of the process seen above, the partially renatured mutein may be purified by reverse phase chromatography.

In this case, the suitably diluted solution containing the partially renatured mutein, that is to say partly in dimeric form and partly in monomeric form, can be loaded onto any commercially available chromatography matrix suitable for the use indicated. Preferably, a resin is used that has a granulometry such as to guarantee optimum exploitation of the matrix absorption capacity together with easy packing of the column itself. Examples of these matrixes are the resins RP Source 15 or RP Source 30 (Amersham biosciences). All the balancing, loading, resin washing and elution solutions are hydro-organic solutions comprising different percentages of organic solvent. Examples of these solutions are solutions comprising ethanol, methanol or acetonitryl. Preferably, hydroalcoholic solutions comprising increasing percentages of ethanol are used. Advantageously, the entire reverse phase chromatography process is carried out automatically by a computerised system operating under the control of a suitable program, e.g. the FPCL Director Software system (Amersham biosciences).

When two or more purification techniques are used one after the other, the mutein may be obtained in a highly purified active form, that is to say with the protein comprised essentially in dimeric form, and without any contamination by the monomeric form. The product obtained in this way comprises not less than 98.5% of the active form, preferably not less than 99.5%. The residual monomeric form does not exceed 1.5%. Given that the mutein is chemically stable, all multimerisation products are limited to traces. The pure protein obtained according to the method described above may be subjected to further processing steps, for example membrane ultrafiltration. In this case the product is filtered on a membrane with a filtration limit (cut-off) lower than or equal to 30 kD and subjected to diafiltration against water acidulated with TFA until reaching a dilution factor of $1:10^6$. The final product obtained in this way may be adequately formulated with lyophilisation additives and lyophilisate to preserve biological activity at optimum levels. In a practical embodiment of the invention, the mutein can be suitably extracted, isolated and purified in accordance with the purification process described in international patent application PCT/IT02/00065 (Geymonat) to purify the wild type PLGF-1 protein, adapting the operating conditions if necessary.

The chemical stability of PLGF-1 muteins according to the invention has been evaluated in tests in which the lyophilised mutein and the wild type PlGF-1 protein were solubilised in saline solution or formulated in a gel and stored at a temperature of 4-8° C. for periods of 40, 170 and 210 days. The results reported below clearly indicate that the mutein in its active dimeric form is stable at all the concentrations analysed (20, 5 and 1 mg/ml), in that it does not tend to precipitate or multimerise, indeed the concentration is found to remain at the initial values. On the contrary, the concentration of the dimeric form of the wild type protein decreases drastically after only a few days.

The muteins according to the invention show, along with an improved chemical/biological stability, an angiogenic activity comparable with that of the wild type PLGF-1 protein. This activity makes the PLGF-1 muteins according to the invention suitable for all therapeutic and cosmetic applications of natural PLGF-1 currently known from the prior art.

The angiogenic action of the PLGF-1 muteins of the invention has been determined using known techniques, carried out in vivo or in vitro. In particular the rabbit cornea vascularization test or the chicken chorioallantoid membrane vascularization test (CAM) were used, as described by Maglione et al. "Il Farmaco", 55, 165-167 (2000).

A second method used to evaluate cutaneous vascularization is computerised morphometric analysis of samples of animal skin, as described by Streit et al. (Proc. Natl. Acad. Sci. USA 1999, December 21, 96(26), pages 14888-14893). Cutaneous sections isolated from laboratory animals, treated or untreated according to the present invention, were immuno-histochemically coloured using monoclonal anti-CD31 antibodies for the animal used. The sections treated in this way were analysed under an electron microscope to evaluate the number of blood vessels per mm2, their average dimensions and the relative area occupied by them. The angiogenic effect of the muteins on the myocardial tissue and in particular in the case of ischemia or myocardial infarct was evaluated on an animal model of cardiac ischemia as described by Maglione et al. (supra).

The activity of the muteins according to the invention in treatment of scleroderma was evaluated on an animal model as described by Yamamoto T. et al. in Arch. Dermatol. Res. November 2000, 292(11), pages 535 to 541. A state of scleroderma is induced in C3H mice with bleomycin (100 mcg/ml) injected daily subcutaneously for 3 weeks. After 3 weeks, the animals are sacrificed and samples of skin from the treated areas are subjected to histological analysis. The effect of the treatment underlines histological events that can be attributed to cutaneous sclerotisation induced by the bleomycin and, in particular, skin thicknening and high hydroxiproline levels.

The results reported below underline the effectiveness of the PLGF-1 muteins according to the invention in the treatment of all those pathological or natural degenerative states that area subject to improvement following an increase in vascularization of the areas involved. A first application is the preventive or curative treatment of ischemia and damage following ischemic events. Conditions liable to be suitable for treatment are ischemia of the myocardial tissue, myocardial infarct, ischemic ictus and chronic myocardial diseases, cerebral ischemia and ischemic ictus, intestinal ischemia, peripheral ischemia of the limbs. A second therapeutic application is treatment of scleroderma. This is a disease that involves the microvascular system, the cutaneous and subcutaneous connective tissue and the connective tissue of internal organs. The disease induces activation of the fibroblasts and excessive production and tissue and perivasal deposit of collagen, which contributes heavily towards the formation of fibrosis and calcification areas, and therefore to the appearance of the symptoms induced by the disease. In particular it can be seen under capillaroscopy that large amounts of sclerotised collagen surround the skin vessels, causing restriction of the vessel lumen. A circumscribed scleroderma with cutaneous involvement can be distinguished, characterised by hardening and thickening of the skin due to excessive and inadequate deposit of collagen, and a progressive systemic scleroderma in which the blood vessels are associated with the cutaneous fibrosis, along with a systemic sclerosis with lesions to the viscera. The skin, above all that of the fingers and hands, is seen to be hardened, thickened and oedematous. The disease is also present at myocardial level with cardiac insufficiency, and at pulmonary, gastrointestinal, renal and osteo-muscular system level. Some patients also develop erosive arthropathies induced by cutaneous fibrosis, which greatly complicate the mobility of joints. Maglione et al. have reported (Italian patent application RM2002A000119) with regard to the wild type PLGF-1 factor, that the promotion of angiogenesis, in particular in the skin, as a result of treatment with compositions containing PLGF-1 has a beneficial effect on the general state of neomycin-induced sclerosis in mice. The same results were observed on animals in which a state of scleroderma had previously been induced and treated with muteins according to the invention.

A third therapeutic application is treatment supporting healing processes in burns, ulcers and internal or cutaneous wounds, particularly during the post-operative steps.

A further application according to the invention relates to treatment of the phenomena typical of skin ageing. This treatment, although considered essentially cosmetic, has therapeutic implications when taking into consideration the precocious deterioration of cutaneous tissue due to prolonged exposure to sunlight (photo-ageing), to radiation of other types or to aggressive environmental/atmospheric agents.

Examination of samples of photo-damaged skin under an electron microscope reveals a typical microvascular morphology that is characterised, among other things, by the presence of capillaries that are pathologically dilated and wrapped with elastin or surrounded by a dense amorphous material. It has been observed that stimulation of new skin vascularization generates, in both naturally and precociously aged skin, a modulating effect on the extra-cellular matrix responsible for skin tone and thickness. The increased capillary vascularization is accompanied by an increase in the fibroblasts and the production of new collagen, followed by a general improvement in the appearance of the skin.

A further application of the compounds of the invention relates to hair loss.

In effect the improved skin vascularization, specifically in the perifollicular area, is accompanied by modulation of the growth of cutaneous appendages (head hair, body hair, etc.) in the sense of prevention of hair loss and promotion of its regeneration. The anagenic phase, which corresponds with the hair growth phase, is accompanied by a natural increase in vascularization of the hair follicle. The local angiogenic action promotes this vascular increase and the consequent growth of the hair. Computerised morphometric analysis of sections of skin proximal to the piliferous follicles of animals treated with the compositions of the invention have shown not only an increase in the dimensions of the hair lumen and hair density, and therefore a general increase in perifollicular vascularization, but also an increase in the dimensions of the hair bulb and the diameter of the hair itself.

The effect of preventing hair loss of promoting re-growth can be applied not only in the case of natural loss, but also in the case of loss following clinically significant states such as alopecia, hormone disorders, chemotherapy, radiotherapy or medicaments administration.

The above identified therapeutic indications relate to direct, systemic or local administration of a mutein of the PLGF-1 factor. However, the muteins of the invention can also be used to produce antibodies, polyclonal, monoclonal or functionally active fragments capable of recognising the endogenous PLGF-1 factor, specifically those regions of the sequence of amino acids containing the bonding site for PLGF-1 and the receptor. Antibodies of this type are capable of neutralising the angiogenic activity of PLGF-1 and find application in treatment of all those conditions characterised by pathological angiogenesis. Examples of these conditions are inflammatory disorders such as rheumatoid arthritis or asthma, oedema, pulmonary hypertension and the formation and development of tumour tissue. The antibodies themselves can be used as immuno-diagnostic reagents in methods for qualitative and quantitative determination of endogenous PLGF-1 production. These reagents find application in diagnosis of all those pathological states accompanied by abnormal production of PLGF-1, such as the formation and development of tumour tissue.

Antibodies or fragments thereof capable of recognising the PLGF-1 muteins are prepared following techniques well known to the man skilled in the art, e.g. following the techniques described in application WO-A-01/85796 for the production of antibodies specific for the wild type PLGF-1 protein.

The present invention likewise relates to pharmaceutical compositions containing the muteins described above or the corresponding neutralising antibodies as active agents or as diagnostic reagents.

Any formulation suitable for systemic or local administration may be used according to the invention. In particular, the PLGF-1 factor may be administered parenterally with a systemic or local effect, or topically on the skin or mucosa with a mainly local effect. A systemic effect is mainly obtained by intravenous administration, although intraperitoneal or intramuscular administration is also possible. A local effect is obtained by topical, or intramuscular, subcutaneous, interarticular parenteral administration. The PLGF-1 muteins may likewise be administered at local level by electrotransport of ionophoresis. Subcutaneous implants can likewise be used when delayed release is required over a period of time. Oral administration of the factor is also possible, although it is less strongly recommended in view of the delicate nature of the active product.

Compositions for systemic or local parenteral use include solutions, suspensions, liposome suspensions, W/O or O/W emulsions. Compositions for topical use include solutions, lotions, suspensions, liposome suspensions, W/O, O/W, W/O/W, O/W/O emulsions, gels, ointments, cremes, pomades and pastes. In a preferred embodiment the active substance is formulated in lyophilised form, mixed with suitable lyophilisation additives and ready to be resolubilised using therapeutically acceptable diluents. Lyophilisation additives that can be used are: buffers, polysaccharides, saccharose, mannitol, inositol, polypeptides, amino acids and any other additive compatible with the active substance. In a preferred embodiment of the invention, the active substance is dissolved in a phosphate buffer ($NaH_2PO_4$/$H_2O$—$Na_2HPO_4$/$2H_2O$) in an amount such that the mutein/phosphate ratio after lyophilisation is comprised between 1:1 and 1:2. Suitable diluents for parenteral use are: water, saline solution, sugar solutions, hydro-alcohol solutions, oily diluents, polyoils, such as glycerol, ethylene or polypropylene glycol, or any other diluent compatible with the administration method in terms of sterility, pH, ionic strength and viscosity.

In the case of emulsions or suspensions the composition may contain suitable surfactant agents of a non-ionic, zwitterionic, anionic or cationic type commonly used in the formulation of medications. Hydrophilic O/W or W/O/W emulsions are preferable for parenteral/systemic use, whereas lipofillic W/O or O/W/O emulsions are preferable for local or topical use.

Furthermore, the compositions of the invention may contain optional additives such as isotonic agents, such as sugars or polyalcohols, buffers, chelating agents, antioxidants, antibacterial agents.

The compositions for topical use include liquid or semi-solid forms. The former comprise solutions or lotions. These can be aqueous, hydro-alcoholic, such as ethanol/water or alcoholic and are obtained by solubilisation of the lyophilised substance.

Alternatively, solutions of the active substance can be formulated as gels by addition of known gelling agents such as: starch, glycerine, polyethylene or polypropylene glycol, poly(meth)acrylate, isopropyl alcohol, hydroxystearate, CARBOPOL®.

Other types of compositions for topical use are, emulsions or suspensions in the form of pomades, pastes and creams. W/O emulsions are preferred, as they provide faster absorption. Examples of lipophillic excipients are: liquid paraffin, anhydrous lanolin, white vaseline, cetylic alcohol, stearylic alcohol, vegetable oils, mineral oils. Agents that increase the skin permeability, so as to facilitate absorption may advantageously be used. Examples of these agents are physiologically acceptable additives such as polyvinyl alcohol, polyethylenglycol or dimethylsulfoxide (DMSO).

Other additives used in the topical compositions are isotonic agents, such as sugars or polyalcohols, buffers, chelating agents, antioxidants, antibacterial agents, thickening agents, dispersing agents.

Compositions for local or systemic use with delayed release over a period of time may equally be used, and these include polymers such as polylactate, poly(meth)acrylate, polyvinyl-pyrrolidone, methylcellulose, carboxymethylcellulose and other substances known in the art. Slow-release compositions in the form of subcutaneous implants based, for example, on polylactate or other biodegradable polymers may also be used.

Although the active substance is already stable in itself and is preferably packed in lyophilised form, the pharmaceutical compositions may advantageously comprise additionally stabilising substances for the PLGF-1 muteins in the active dimeric form. Examples of these substances are: Cysteine, Cysteamine, or glutathione.

Dosage of the mutein depends on the administration route and on the formulation chosen. For parenteral administration the amounts vary from 1 mcg/Kg/day to 500 mcg/Kg/day, preferably from 10 mcg/Kg/day to 200 mcg/Kg/day. These administrations are obtained with pharmaceutical compositions comprising from 50 mcg to 30 mg per unit dose, preferably from approximately 500 mcg to 10 mg per dose. For therapeutic topical application amounts varying from 0.1 mg to 10 mg per gram of composition have proved effective. Local cosmetic compositions for treatment of skin ageing or hair loss comprises preferably from 0.01 mg to 0.09 mg of active substance per gram of composition.

The duration of the treatment varies according to the pathology or the effect required. In the case of treatment of scleroderma the application period varies from 1 day to 12 months, according to the severity of the pathology. In the case of treatment for natural or precocious skin ageing, the application period varies from 1 to 400 days, preferably for at least 30 days. In the case of treatment to prevent hair loss or to promote re-growth of hair the application period likewise varies from 1 to 400 days.

The invention is described in the following by means of examples whose purposes is solely illustrative and is not limiting.

EXAMPLE 1

Synthesis of the cDNA Encoding the mutein.

The PlGF-1 MUTEIN, which we have called PlGF-1CG, was generated by mutation of the thymidine (T) N°382 (sequence SEQ ID NO:1) into guanidine (G). In this way the TGC codon, nucleotides 382-384 of the sequence indicated above, encoding a cysteine was transformed into GGC encoding a glycine.

From an amino acid point of view the cysteine mutated into glycine in the mutein PlGF-1CG is in position 125 of the sequence SEQ ID NO:2.

For synthesis of the DNA encoding the mutein, the PCR (polymerase chain reaction) technique was applied. The expression vector pET3PLGF1 encoding the protein methionyl PlGF-1 without signal peptide (EP-A-0 550 519) was used as a template for the PCR. In practice this is the wild type PLGF-1 protein without the first 18 amino acids (signal peptide) and with a methionine in position 1 (N-terminal) (SEQ ID NO:2). The oligonucleotides used as primers are the following:

oligo1 (forward primer) having the sequence 5'-CTGGC GCATATGCTGCCTGCTGTGCCC-3=. This contains an NdeI site (underlined) and the start codon (in bold);

oligo2 (reverse primer) having the sequence 5'-GGTTAC-CTCCGGGGAACAGCATCGCCGCCCC-3'. This contains a mutation T→G (nucleotide underlined and in bold) that transforms the TGC codon, encoding a cysteine, into the GGC codon (bold) encoding a glycine.

The nucleotide chain obtained after PCR performed with a BioRad Gene Cycler was subjected to a completion reaction (fill-in) and, subsequently, digested with the restriction enzyme NdeI. The fragment obtained, with NdeI/"blunt" ends, was cloned in corresponding NdeI/"blunt" ends of the prokaryotic expression vector pET3 according to standard protocols. In this way the plasmid pET3PLGF1CG encoding the PLGF-1 mutein known as PLGF-1CG was created.

This plasmid was used according to known techniques to transform the strain of *E. coli* [B12(DE3)pLysS] (Promega Corporation USA) and produce the host strain [B12(DE3) pLysS PLGF-1CG].

The construction technique used for this plasmid is outlined in FIG. 5.

EXAMPLE 2

Production, Extraction and Purification of the Mutein PLGF-1CG

The micro-organism [Bl21(DE3)pLysS PLGF-1CG] has been cultivated in a fermenter using as a culture medium the solution SBM comprising:

| Solution A (per 1 liter) | | |
|---|---|---|
| Bacto yeast extract(Difco) | | 34 g |
| Ammonium sulphate | | 2.5 g |
| Glycerol | | 100 ml |
| H$_2$0 | q.s. to: | 900 ml |
| Solution B (10 X) (per 100 ml) | | |
| KH$_2$PO$_4$ | | 1.7 g |
| K$_2$HPO$_4$—3H$_2$O | | 20 g |
| or | | |
| K$_2$HPO$_4$ | | 15.26 g |
| H$_2$0 | q.s. to: | 100 ml |

Solutions A and B are mixed in sterile form at the time of use.

Expression is induced by means of IPTG (isopropyl-β-D-thiogalactopyranoside) 1 mM.

Fermentation is preceded by a pre-inoculation step. A tube of lyophilised micro-organism is taken and suspended in 1 ml of SBM+100 µg/ml Ampicillin+34 µg/ml chloramphenicol, the suspension is further diluted and incubated at 37° C. for one night. After dilution in the same SBM solution additioned with Ampicillin and chloramphenicol, the pre-inoculate is divided into 4 Erlenmeyer flasks.

The content of each Erlenmeyer flask is incubated at 37° C. for 24 hours. The contents of the 4 Erlenmeyer flasks are mixed and the $OD^{600}$ are read, diluting 1/20 in water (50 µl+950 µl water).

An established pre-inoculation volume is then centrifuged for 10 min. at 7,500×g at 4° C. in sterile tubes. The bacteria are then re-suspended in 20 ml SBM+200 µg/ml Ampicillin+ 10 µg/ml chloramphenicol per litre of fermentation, by stirring at 420 rpm at R.T. for 20 minutes.

Fermentation is carried out in SBM solution containing 200 ug/ml ampicillin, 10 µg/ml chloramphenicol and a suitable amount of anti-foaming agent, at a temperature of 37° C. and in the presence of (30%) dissolved $O_2$ and at a pH value of between 6.4 and 7.4.

Induction is commenced when the culture medium has reached an optical density at 600 nm ($OD^{600}$) of between 16-20 units.

The inducing agent used is IPTG 1 mM in the presence of 10% dissolved $O_2$ (with respect to air saturation). The duration of the induction is approximately 3 hours. Induction is controlled by performing SDS-PAGE electrophoresis, loading 20 µl of pre- and post-induction solution previously boiled.

The culture medium containing the induced bacteria is then centrifuged at 7,500×g for 10 min. or at 3000×g for 25 min. at 4° C. and the supernatant is discarded.

The bacterial cells are subsequently subjected to lysis followed by extraction and purification of the inclusion bodies. Bacterial lysis is performed by means of 2 freezing/thawing cycles at −80/37° C. in a lysis solution containing 1 mM $Mg_2SO_4$+20 mM Tris-HCl pH8+1% Triton X100.

The lysis mixture is incubated at room temperature for 30 min. under stirring (250 RPM), and then poured into a blender of suitable capacity, diluting with an amount of washing solution, containing 0.5% triton×100+10 mM EDTA pH 8, equivalent to 3 ml per 450 $OD^{600}$ of bacteria.

If necessary, 0.4 µl of undiluted anti-foaming agent are added for each millilitre of sample.

The solution is blended at maximum speed for 1 minute, or until the sample is homogeneous. The contents of the blender are then transferred to a container of suitable capacity, adequately diluted with 6.5 ml of washing solution for every 450 $OD^{600}$ of bacteria, the suspension obtained in this way is centrifuged at 13,000×g for 45 min. at 25° C. and the supernatant discarded.

The entire washing process is repeated for a number of cycles until obtaining a final pellet containing the inclusion bodies of the expressed protein.

Following this, the pellet containing the inclusion bodies is solubilised in 7 ml of denaturing buffer BD (8M urea, 50 mM Tris pH 8, Ethylendiamine 20 mM), then the solution is diluted to bring the final urea concentration to 5M. Renaturation of the protein is carried out on the solution obtained in this manner, by addition of reduced glutathione (final concentration equivalent to 1.25 mM) and oxidised glutathione (final concentration equivalent to 0.5 mM), and incubation at 20° C. for 18-20 hours under stirring.

At the end of the incubation period it is centrifuged for 10 min. at 20° C., 10,000×g, and filtered through 0.45 or 0.8 µm filters.

The mutein in renatured form, i.e. in dimeric form, is subjected to purification by anion exchange chromatography.

The mutein solution is loaded onto Q-sepharose Fast Flow resin (Amersham-biosciences) equilibrated with buffer A (20 mM Ethanolamine-HCl pH 8.5) and eluted, after washing, with 20% buffer B (buffer A+1M NaCl), corresponding to an NaCl concentration of 200 mM.

The partially purified mutein is brought up to a higher degree of purity by reverse phase chromatography. For this purpose the ion exchange chromatography elution peak is diluted with a solution containing TFA and ethanol so that the sample is diluted 1.5 times and contains 15% ethanol and 0.3% TFA. The addition of these substances enhances bonding of the mutein to the reverse phase resin.

The solution is loaded onto RP Source resin (Amersham-Bioscience) with an average diameter of 15 or 30 micron balanced with a solution containing 40% Ethanol and 0.1% TFA. The washing solution removes the monomeric form of the mutein, whereas the dimeric form is eluted in an increasing ethanol gradient until reaching a percentage of 70% ethanol.

The chromatography purification process is monitored controlling the absorption at 280 nm of the eluted fractions.

The dimer solution obtained in this way is stored at −20° C., and subsequently ultradiafiltered and lyophilised according to known techniques.

EXAMPLE 3

I Stability Study on the PLGF-1CG Mutein Carrying the Substitution Cys 125 Gly

The PlGF-1CG mutein was solubilised in saline solution at theoretical concentrations of 20, 5 and 1 mg/ml. Simultaneously the PlGF-1 protein (without mutation) was also solubilised in saline solution at a concentration of 20 mg/ml. All the samples were stored in the refrigerator (4-8° C.) for up to 40 days.

The actual concentration was determined by calculating the average of the values obtained from 3 suitable independent dilutions. The method used was spectrophotometry using a wavelength of 280 nm and knowing that an absorbency of 1 OD (optical density), measured a cuvette with a standard 1 cm optical path, corresponds to a concentration of PlGF-1 and PlGF-1CG equivalent to 1 mg/ml. During the days following the start of the experiment (time 0 on table 1), before carrying out the suitable dilutions to determine concentration, an aliquot of each sample was centrifuged at 13,000 rpm in an ALC 4212 microcentrifuge for 10 minutes and the supernatant was used for subsequent analysis. In this way, possible precipitants were eliminated and, consequently, the results referred to the protein remaining in the solution only.

The results of this study are illustrated in table 1, and clearly show that the mutein, at all the concentrations analysed (20, 5 and 1 mg/ml), and at least up to 40 days, is stable in that it does not tend to precipitate, so much so that the concentration is found to remain within the initial values. Vice versa, after just 4 days storage only 7.8% of the protein without mutation, stored at a concentration of 20 mg/ml at the same conditions as the mutein, remains in the solution. This value drops still further (5.5%) after 12 days. It is important to note that even after 24 hours of storage at 4-8° C. abundant precipitation of the PlGF-1 protein without mutation is already seen.

TABLE 1

| Time stored at 4-8° C. (days) | Average concentration (mg/ml) | | | | | | | |
|---|---|---|---|---|---|---|---|---|
| | PlGF-1CG 20 mg/ml | S.D. | PlGF-1CG 5 mg/ml | S.D. | PlGF-1CG 1 mg/ml | S.D. | PlGF-1 20 mg/ml | S.D. |
| 0 | 20.38 | 1.00 | 5.43 | 0.04 | 1.07 | 0.02 | 20.14 | 0.18 |
| 4 | 19.69 | 0.57 | 5.25 | 0.27 | 0.98 | 0.08 | 1.57 | 0.10 |
| 12 | 20.46 | 0.54 | 5.28 | 0.19 | 1.00 | 0.01 | 1.11 | 0.01 |
| 26 | 20.72 | 0.33 | N.A. | | N.A. | | N.A. | |
| 40 | 20.32 | 0.75 | N.A. | | N.A. | | N.A. | |

S.D. = Standard Deviation
N.A. = Not Analysed

Figure 1:
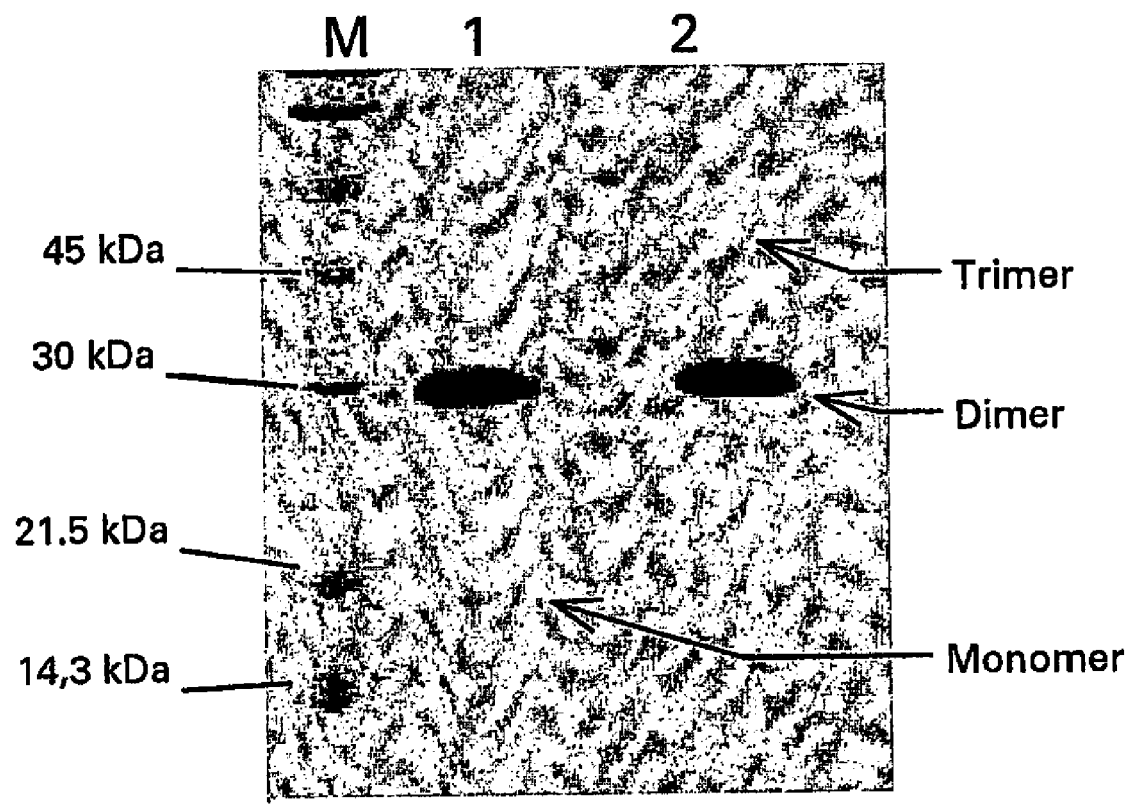
FIG. 1: The figure shows the SDS-PAGE electrophoretic profile of PLGF-1CG after re-suspension in physiologic solution at 20 mg/ml and storage at 4-8° C. for 40 days. The profile is compared with the profile for the mutein immediately after solubilisation.

The electrophoresis profile (monomer-dimer-polymer composition) for the PlGF-1CG mutein (FIG. 1) is also substantially stable at the conditions indicated above. In effect, SDS-PAGE electrophoresis in non-reducing conditions of the PlGF-1CG protein, solubilised in saline solution at 20 mg/ml and frozen (control, line 1 of FIG. 1) or stored at 4-8° C. for 40 days (sample, line 2 of FIG. 1), substantially reveals only minimum alterations, represented by disappearance of the tiny monomeric portion and by the formation of an extremely low amount of trimer (<0.5% of the dimer).

EXAMPLE 4

II Stability Study on the PLGF-1CG Mutein Formulated in Gel

The PlGF-1CG mutein and the non-mutated PlGF-1 protein were solubilised at a concentration of 0.2 mg/ml in a gel is composed as follows:

| | |
|---|---|
| CARBOPOL 940 = | 1% P/V |
| Sodium Acetate pH 4.4 = | 15 mM |
| EDTA non pHated disodium salt = | 0.04% P/V |
| Methyl paraben = | 0.05% P/V |

Brought up to, a pH of between 5.5 and 6 using NaOH/ acetic acid.

The 2 gels were stored at 4-8° C. At various times a portion, in duplicate, of the 2 gels (approximately 0.2 ml) was taken and weighed on the analytical balances.

The weighed samples were additioned with a volume, expressed in microlitres, of non reducing 2× Sample Buffer equivalent to the weight, expressed in milligrams, of the gel portion.

After vortex stirring for 10 minutes and centrifuging at 13,000 rpm (ALC 4214 microcentrifuge) for a further 10 minutes, the supernatant was withdrawn. This was centrifuged again and the new supernatant was removed. A portion of the latter, together with quantity standards, were analysed by non reducing SDS-PAGE electrophoresis. After colouring, the electrophoresis gels were analysed using a densiometer to find the concentration of the dimeric form of the samples analysed.

The results obtained at various times and expressed as percentage dimer with respect to that present at time zero, are indicated in Table 2 and expressed in graph form in FIG. 2. From this data it can be seen that, whereas the mount of PlGF-1CG dimer remains constant until the end of the 170 days analysed, that of PlGF-1 drops to 71% after 150 days, and to 55% after 210 days.

The electrophoresis profile (monomer-dimer-polymer composition) also shows that the PlGF-1CG mutein is substantially sable at the conditions indicated above (FIG. 3). In effect, SDS-PAGE electrophoresis in non-reductive conditions of the PlGF-1CG protein, solubilised in carbopol at 0.20 mg/ml and frozen (control, line 2 of FIG. 3) or stored at 4-8° C. for 170 days (sample, line 1 of FIG. 3), does not reveal any polymerisation phenomena. Vice versa, these multimerisation phenomena are clearly evident for the non-mutated PlGF-1 protein, as illustrated in FIG. 4 (compare line 1—protein stored at 4°-8° C. for 150 days, with line 2—frozen protein).

TABLE 2

| | % dimer | |
|---|---|---|
| Time stored at 4-8° C. (days) | GEL PlGF-1CG (mutein) | GEL PlGF-1 |
| 0 | 100.00 | 100.00 |
| 30 | 108.00 | N.A. |
| 57 | N.A. | 83.40 |
| 119 | N.A. | 72.70 |
| 133 | 98.70 | N.A. |
| 150 | N.A. | 71.10 |
| 170 | 101.50 | N.A. |
| 210 | N.A. | 54.90 |

N.A. = not analysed

EXAMPLE 5

Evaluation of the angiogenic activity of the PLGF-1CG mutein

The antiogenic activity of the PLGF-1CG mutein, of the wild type PLGF-1 factor and, as a positive reference, of the basic fibroblast growth factor (bFGF) were compared using the chicken chorioallantoid membrane vascularization test (CAM) already described by Maglione et al. ("Il Farmaco" supra). Various amounts of mutein and wild type factor (between 0 and 3 mcg/sponge) were absorbed on 1 $mm^3$ gelatine sponges, subsequently implanted on the surface of CAMs. After 12 days, the CAM regions in contact with the samples were sectioned, coloured and the angiogenic effect was quantified using the morphometric technique known as "point counting". Specifically, the CAM sections were analysed under a microscope on a grid with 144 intersection points and the results were expressed as the percentage of the intersection points occupied by the capillaries on a transversal section (percentage of the area that is vasculised). The results, illustrated in FIG. 6, show essentially equivalent angiogenic activity for the mutein and the wild type factor.

EXAMPLE 6

Evaluation of the Effect of the PLGF-1CG Mutein on Isoprenaline-Induced Cardiac Ischemia The effect of the PLGF-1CG mutein on cardiac ischemia and infarct was evaluated on ischemia induced in an animal model by means of isoprenaline, as described by Maglione et al. (supra) in relation to the wild type factor. The experiment was carried out on rabbits, which were treated with a single daily dose of 160 mcg/Kg of mutein or with equivalent volumes of excipient only, administered intravenously on days 1 to 5. The Isoprenaline was administered subcutaneously on days 1 and 2. The characteristics typical of the electrocardiogram (ECG) indicating the main ischemic damage, such as inversion of the T wave, widening of the S wave and prominence of the Q wave, are decidedly more marked in animals treated with the excipient alone, with respect to animals treated with the mutein under examination. Variations in the ECG of treated and untreated animals were evaluated on a point scale ranging from zero to six, as reported below: 0, no lesion; 1, prominence of the S wave; 2, prominence of the T wave; 3, depression of the descending arm of the T wave; 4, widening of the S wave; 5, inversion of the T wave; 6, prominence of the Q wave. The total area under the curve defined by the ECG points during the 5 days of the test was likewise calculated for treated and untreated animals. The results are illustrated in FIG. 7 and show a significant reduction in the ischemic damage in animals treated with the PLGF-1CG mutein. The results underlined by the electrocardiographic profile were confirmed by macro and microscopic observation of the ischemic tissues. Said examination shows the presence of ischemic lesions and histological alterations of moderated severity with respect to the ones observed in the cardiac tissue of animals treated with the excipient only.

EXAMPLE 7

Evaluation of the Effect of the PLGF-1CG Mutein on Neomycin-Induced Scleroderma

In this study the animal scleroderma model described by Yamamoto et al. (supra) was used.

A first group of C3H mice was treated with bleomycin (100 mcg/ml) injected daily subcutaneously for 3 weeks. Three other groups of C3H mice were likewise treated as above, but 0.1, 1 and 10 mcg/ml of the PlGF-1CG mutein was added to the daily injection, respectively. After 3 weeks treatment, the animals were sacrificed and samples of skin from the treated areas were taken and subjected to histological analysis. The effect of the treatment with PlGF-1CG at 1 and 10 mcg/ml, but not at 0.1 mcg/ml, underlines a significant reduction in histological events that can be attributed to cutaneous sclerotisation induced by the bleomycin. In particular, skin thickneining and hydroxiproline levels were significantly decreased with respect to the mice treated with bleomycin alone.

EXAMPLE 8

Pharmaceutical Compositions i) Solution for Parenteral Use:

58 milligrams of lyophilised mutein, containing 25 mg pure FLGF-1CG and 33 mg phosphate buffer (10 mg NaH2PO4/H2O and 23 mg Na2HPO4/2H2O), and approximately 125 ml saline solution for parenteral use, are packed separately in vials prepared to allow mixing of the lyophilised product with the diluent immediately prior to use. The concentration of active substance resulting after solubilisation is approximately 0.2 mg/ml.

ii) Topical Composition in Gel Form:

An amount of lyophilised substance containing 10 mg active substance is carried in 20 ml of 10% ethanol hydroalcoholic solution containing 20% DMSO. The solution is then additioned with a suitable gel excipient containing the following ingredients: 1% Carbopol 940, sodium acetate 15 mM (pH 4.4), 0.04% p/v disodium EDTA, 0.05% p/v methyl paraben with a final pH comprised between 5.5 and 6.

What is claimed is:

1. A mutein of the monomeric form of a mammalian type 1 Placental Growth Factor (PLGF-1) comprising a polypeptide sequence that differs from said mammalian PLGF-1 by a substitution or an elimination of a cysteine residue (Cys) corresponding to position 125 of SEQ ID NO: 2, wherein the mutein retains an ability to form a PLGF-1 dimer, and wherein said substitution or elimination prevents multimerisation of said monomeric form, and wherein said mutein has angiogenic activity.

2. The mutein according to claim 1, wherein the Cys residue is replaced by a glycine residue (Gly).

3. The mutein according to claim 1 in the form of a pre-protein or a mature protein.

4. The mutein according to claim 1 that is at least 98.5% in dimeric form.

5. A nucleotide sequence consisting of a DNA sequence encoding the PLGF-1 mutein according to claim 1.

6. The nucleotide sequence according to claim 5 wherein a TGC codon in position 382-384 in the sequence encoding the mature wild type PLGF-1 is eliminated or modified.

7. The nucleotide sequence according to claim 6 in which the thymidine base in position 382 of the sequence SEQ ID NO:1, or derivatives thereof caused by degeneration of the DNA, is substituted by a guanidine base.

8. An expression system comprising the nucleotide sequence according to claim 5, flanked by untranslated sequences for control and regulation of expression.

9. The expression system according to claim 8, that is an expression system inducible in bacterial cells.

10. The expression system according to claim 9, wherein the expression is under the control of an inducible promoter.

11. The expression system according to claim 8 comprising a T7 phage RNA-polymerase expression system, wherein expression is induced by means of lactose, isopropyl-β-D-thiogalactopyranoside (IPTG) or a functional equivalent.

12. A host cell transformed by means of the expression system according to claim 8.

13. The cell according to claim 12, that is a bacterial cell.

14. The bacterial cell according to claim 13 that is derived from a strain of E.coli.

15. A process for the production of the nucleotide sequence according to claim 5 comprising producing the DNA sequence encoding the PLGF-1 mutein by polymerase chain reaction (PCR), wherein the oligonucleotide of sequence SEQ ID NO:3 is used as a 5'-3' (forward) primer and the oligonucleotide of sequence SEQ ID NO:4 is used as a 5'-3' (reverse) primer.

16. The process according to claim 15 in which the DNA sequence encoding the PLGF-1 protein without a signal protein is used as a template in the polymerase chain reaction.

17. A process for the production and extraction of a mutein of the factor PLGF-1 comprising: cultivating the host cell according to claim 12 in a suitable culture medium, inducing the expression of the protein using a suitable inducer, isolating and lysing cells and extracting the mutein from the lysis mixture.

18. The process according to claim 17 comprising culturing the cells until reaching an optical density (O.D.) of the culture medium between 0.2 and 50 units, at 600 nm before inducing the expression.

19. The process according to claim 18 further comprising isolating the inclusion bodies released during lysis, solubilizing the inclusion bodies in a denaturing buffer and optionally homogenizing or sonicating.

20. The process according to claim 19, further comprising diluting the solution of solubilized inclusion bodies and renaturing the proteic material in dimeric form by addition to the solution an oxidizing-reducing agent.

21. The process according to claim 20, further comprising at least one purification step selected from the group comprising ion exchange chromatography, reverse phase chromatography and ultrafiltration.

22. A pharmaceutical composition comprising the mutein according to claim 4 and a pharmaceutically acceptable excipient.

23. A Pharmaceutical composition according to claim 22 for parenteral, topical, oral, nasal or implant use.

24. A Cosmetic composition containing the mutein according to claim 4 and a cosmetically acceptable excipient.

25. A method for the preparation of the pharmaceutical composition according to claim 22, comprising associating the PLGF-1 mutein with a pharmacologically acceptable excipient and with other usual additives.

26. A method for the preparation of the cosmetic composition according to claim 24, comprising associating the PLGF-1 mutein with a cosmetically acceptable excipient and with other usual additives.

* * * * *

SEQUENCE LISTING

```
<160> NUMBER OF SEQ ID NOS: 4

<210> SEQ ID NO 1
<211> LENGTH: 418
<212> TYPE: DNA
<213> ORGANISM: Homo sapiens
<220> FEATURE:
<221> NAME/KEY: CDS
<222> LOCATION: (10)..(408)
<223> OTHER INFORMATION: DNA coding for signal peptide is absent.
      Nucleotides 10-408 code for amino acids 19-149 of protein
      disclosed in Calim 1 of EP 0550 519.

<400> SEQUENCE: 1 ctggcgcat atg ctg cct gct gtg ccc ccc cag cag tgg gcc ttg tct gct        51
          Met Leu Pro Ala Val Pro Pro Gln Gln Trp Ala Leu Ser Ala
          1               5                   10 ggg aac ggc tcg tca gag gtg gaa gtg gta ccc ttc cag gaa gtg tgg          99
```

```
Gly Asn Gly Ser Ser Glu Val Glu Val Val Pro Phe Gln Glu Val Trp
 15                  20                  25                  30 ggc cgc agc tac tgc cgg gcg ctg gag agg ctg gtg gac gtc gtg tcc      147
Gly Arg Ser Tyr Cys Arg Ala Leu Glu Arg Leu Val Asp Val Val Ser
                 35                  40                  45 gag tac ccc agc gag gtg gag cac atg ttc agc cca tcc tgt gtc tcc      195
Glu Tyr Pro Ser Glu Val Glu His Met Phe Ser Pro Ser Cys Val Ser
             50                  55                  60 ctg ctg cgc tgc acc ggc tgc tgc ggc gat gag aat ctg cac tgt gtg      243
Leu Leu Arg Cys Thr Gly Cys Cys Gly Asp Glu Asn Leu His Cys Val
         65                  70                  75 ccg gtg gag acg gcc aat gtc acc atg cag ctc cta aag atc cgt tct      291
Pro Val Glu Thr Ala Asn Val Thr Met Gln Leu Leu Lys Ile Arg Ser
     80                  85                  90 ggg gac cgg ccc tcc tac gtg gag ctg acg ttc tct cag cac gtt cgc      339
Gly Asp Arg Pro Ser Tyr Val Glu Leu Thr Phe Ser Gln His Val Arg
 95                 100                 105                 110 tgc gaa tgc cgg cct ctg cgg gag aag atg aag ccg gaa agg tgc ggc      387
Cys Glu Cys Arg Pro Leu Arg Glu Lys Met Lys Pro Glu Arg Cys Gly
                115                 120                 125 gat gct gtt ccc cgg agg taa cccaggatcc                               418
Asp Ala Val Pro Arg Arg
            130

<210> SEQ ID NO 2
<211> LENGTH: 132
<212> TYPE: PRT
<213> ORGANISM: Homo sapiens

<400> SEQUENCE: 2

Met Leu Pro Ala Val Pro Pro Gln Gln Trp Ala Leu Ser Ala Gly Asn
 1               5                  10                  15

Gly Ser Ser Glu Val Glu Val Val Pro Phe Gln Glu Val Trp Gly Arg
                 20                  25                  30

Ser Tyr Cys Arg Ala Leu Glu Arg Leu Val Asp Val Val Ser Glu Tyr
             35                  40                  45

Pro Ser Glu Val Glu His Met Phe Ser Pro Ser Cys Val Ser Leu Leu
 50                  55                  60

Arg Cys Thr Gly Cys Cys Gly Asp Glu Asn Leu His Cys Val Pro Val
65                  70                  75                  80

Glu Thr Ala Asn Val Thr Met Gln Leu Leu Lys Ile Arg Ser Gly Asp
                 85                  90                  95

Arg Pro Ser Tyr Val Glu Leu Thr Phe Ser Gln His Val Arg Cys Glu
            100                 105                 110

Cys Arg Pro Leu Arg Glu Lys Met Lys Pro Glu Arg Cys Gly Asp Ala
        115                 120                 125

Val Pro Arg Arg
    130

<210> SEQ ID NO 3
<211> LENGTH: 27
<212> TYPE: DNA
<213> ORGANISM: Artificial Sequence
<220> FEATURE:
<223> OTHER INFORMATION: Forward Primer for human PLGF-1 PCR
      amplification. Nucleotides 7-10 code for NdeI restriction site.
      Hybridises to antisense strand.

<400> SEQUENCE: 3
ctggcgcata tgctgcctgc tgtgccc                                         27
```

```
<210> SEQ ID NO 4
<211> LENGTH: 31
<212> TYPE: DNA
<213> ORGANISM: Artificial Sequence
<220> FEATURE:
<223> OTHER INFORMATION: Reverse primer for PCR PLGF-1 amplification.
      Nucleotide 29 is a C instead of the T present at position 382 of
      SEQ ID NO: 1. T to C subtitution leads to a mutation from Cys to
      Gly in the protein coded.

<400> SEQUENCE: 4
ggttacctcc ggggaacagc atcgccgccc c                                    31
```